US009271968B2

(12) United States Patent
Viscomi et al.

(10) Patent No.: US 9,271,968 B2
(45) Date of Patent: *Mar. 1, 2016

(54) POLYMORPHOUS FORMS OF RIFAXIMIN, PROCESSES FOR THEIR PRODUCTION AND USE THEREOF IN THE MEDICINAL PREPARATIONS

(71) Applicant: ALFA WASSERMANN S.P.A., Alanno (IT)

(72) Inventors: Giuseppe Claudio Viscomi, Sasso Marconi (IT); Manuela Campana, Bologna (IT); Donatella Confortini, Calderara di Reno (IT); Maria Barbanti, Bologna (IT); Dario Braga, Bologna (IT)

(73) Assignee: ALFA WASSERMANN S.P.A. (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/262,612

(22) Filed: Apr. 25, 2014

(65) Prior Publication Data

US 2015/0073007 A1 Mar. 12, 2015

Related U.S. Application Data

(63) Continuation of application No. 13/950,642, filed on Jul. 25, 2013, now Pat. No. 8,741,904, which is a continuation of application No. 13/488,345, filed on Jun. 4, 2012, now Pat. No. 8,518,949, which is a continuation of application No. 11/658,702, filed as application No. PCT/EP2006/001755 on Feb. 27, 2006, now Pat. No. 8,193,196.

(51) Int. Cl.
*A61K 31/395* (2006.01)
*A61K 31/437* (2006.01)
*C07D 498/22* (2006.01)

(52) U.S. Cl.
CPC ............ *A61K 31/437* (2013.01); *C07D 498/22* (2013.01)

(58) Field of Classification Search
CPC .................................................. A61K 31/395
USPC ..................................................... 514/254.11
See application file for complete search history.

(56) References Cited

U.S. PATENT DOCUMENTS

| | | | |
|---|---|---|---|
| 4,341,785 A | 7/1982 | Marchi et al. | |
| 7,585,838 B2 | 9/2009 | Lin et al. | |
| 7,605,240 B2 | 10/2009 | Lin et al. | |
| 7,709,634 B2 | 5/2010 | Kothakonda et al. | |
| 7,928,115 B2 | 4/2011 | Forbes et al. | |
| 8,067,429 B2 | 11/2011 | Gushurst et al. | |
| 8,193,196 B2 | 6/2012 | Viscomi et al. | |
| 8,197,805 B2 | 6/2012 | Lin et al. | |
| 8,227,482 B1 | 7/2012 | Parent et al. | |
| 8,404,704 B2 | 3/2013 | Viscomi et al. | |
| 8,569,326 B2 | 10/2013 | Gushurst et al. | |
| 2009/0082558 A1 | 3/2009 | Kothakonda et al. | |
| 2009/0312357 A1 | 12/2009 | Rao et al. | |
| 2010/0174064 A1 | 7/2010 | Gushurst et al. | |
| 2010/0317681 A1 | 12/2010 | Forbes | |
| 2011/0086871 A1 | 4/2011 | Viscomi et al. | |
| 2011/0105550 A1 | 5/2011 | Gushurst et al. | |
| 2011/0178113 A1 | 7/2011 | Forbes et al. | |
| 2012/0076857 A1 | 3/2012 | Gushurst et al. | |
| 2012/0116071 A1 | 5/2012 | Rao et al. | |
| 2012/0202989 A1 | 8/2012 | Viscomi et al. | |
| 2012/0203000 A1 | 8/2012 | Viscomi et al. | |
| 2012/0207833 A1 | 8/2012 | Parent et al. | |
| 2012/0214989 A1 | 8/2012 | Viscomi et al. | |
| 2012/0264774 A1 | 10/2012 | Parent et al. | |
| 2013/0004576 A1 | 1/2013 | Viscomi et al. | |
| 2013/0066079 A1 | 3/2013 | Gushurst et al. | |
| 2013/0164384 A1 | 6/2013 | Johnson et al. | |
| 2013/0184302 A1 | 7/2013 | Bortey et al. | |
| 2013/0281697 A1 | 10/2013 | Viscomi et al. | |
| 2013/0289269 A1 | 10/2013 | Viscomi et al. | |
| 2013/0310410 A1 | 11/2013 | Viscomi et al. | |
| 2014/0011828 A1 | 1/2014 | Gushurst et al. | |
| 2015/0073007 A1 | 3/2015 | Viscomi et al. | |

FOREIGN PATENT DOCUMENTS

| | | |
|---|---|---|
| EP | 0935417 B1 | 8/1999 |
| EP | 1676847 B1 | 1/2009 |
| EP | 1676848 B1 | 1/2009 |
| EP | 2208730 A1 | 7/2010 |

(Continued)

OTHER PUBLICATIONS

ICH Topic Q 6 A, Specifications: Test Procedures and Acceptance Criteria for New Drug Substances and New Drug Products: Chemical Substances, May 1, 2000, pp. 1-32, European Medicines Agency.
Andreas Hotter, Preparation of Raw Refaximin and of dried raw Rifaximin according to example 1 of EP 1698630—Andreas Hotter, May 29, 2015, pp. 1-6.
Normix, Riassunto Delle Caratteristiche Del Prodotto—Jun. 1, 2000, pp. 1-10.
Normix, Foglietto Illustrativo—Sep. 2012, pp. 1-8.
Arthur Pichler, Analysis Via Powder X-Ray Diffraction of Current Normix Tablets, May 29, 2015, pp. 1-9.
Dana Hoffmann, Rifaximin, Oral Bioavailability Study in Dogs of Four Different Polymorphic Isoforms, Jun. 3, 2015, pp. 1-4.

(Continued)

*Primary Examiner* — Bruck Kifle
(74) *Attorney, Agent, or Firm* — Steinfl & Bruno LLP

(57) ABSTRACT

Crystalline polymorphous forms of the rifaximin (INN) antibiotic named rifaximin δ and rifaximin ε useful in the production of medicinal preparations containing rifaximin for oral and topical use and obtained by means of a crystallization process carried out by hot-dissolving the raw rifaximin in ethyl alcohol and by causing the crystallization of the product by addition of water at a determinate temperature and for a determinate period of time, followed by a drying carried out under controlled conditions until reaching a settled water content in the end product, are the object of the invention.

18 Claims, 2 Drawing Sheets

(56) References Cited

FOREIGN PATENT DOCUMENTS

| | | |
|---|---|---|
| EP | 2210893 A1 | 7/2010 |
| EP | 2420226 A1 | 2/2012 |
| IT | 1154655 | 11/1981 |
| IT | 1349654 | 10/2003 |
| NZ | 20040531622 A | 10/2004 |
| WO | 9000553 A1 | 1/1990 |
| WO | 9200302 A1 | 1/1992 |
| WO | 0214323 A2 | 2/2002 |
| WO | 0236542 A1 | 5/2002 |
| WO | 0243732 A1 | 6/2002 |
| WO | 2005044823 A2 | 5/2005 |
| WO | 2006094662 A1 | 9/2006 |
| WO | 2008035109 A1 | 3/2008 |
| WO | 2008155728 A1 | 12/2008 |
| WO | 2009008006 A2 | 1/2009 |
| WO | 2009108730 A2 | 9/2009 |
| WO | 2010044093 A1 | 4/2010 |
| WO | 2010067072 A1 | 6/2010 |
| WO | 2010148040 A1 | 12/2010 |
| WO | 2011032085 A1 | 3/2011 |
| WO | 2011050397 A1 | 5/2011 |
| WO | 2011051971 A2 | 5/2011 |
| WO | 2011061516 A2 | 5/2011 |
| WO | 2011061519 A2 | 5/2011 |
| WO | 2011061748 A1 | 5/2011 |
| WO | 2011080691 A1 | 7/2011 |
| WO | 2011103120 A1 | 8/2011 |
| WO | 2011103246 A1 | 8/2011 |
| WO | 2011110930 A2 | 9/2011 |
| WO | 2011153444 A1 | 12/2011 |
| WO | 2011156897 A2 | 12/2011 |
| WO | 2012009387 A1 | 1/2012 |
| WO | 2012009388 A1 | 1/2012 |
| WO | 2012035283 A1 | 3/2012 |
| WO | 2012035544 A2 | 3/2012 |
| WO | 2012076832 A1 | 6/2012 |
| WO | 2012109605 A2 | 8/2012 |
| WO | 2012150561 A1 | 11/2012 |
| WO | 2012155981 A1 | 11/2012 |
| WO | 2012156533 A1 | 11/2012 |
| WO | 2012156951 A1 | 11/2012 |
| WO | 2013112809 A2 | 8/2013 |
| WO | 2013185211 A1 | 12/2013 |
| WO | 2014006576 A1 | 1/2014 |
| WO | 2014091432 A1 | 6/2014 |
| WO | 2015014984 A1 | 2/2015 |

OTHER PUBLICATIONS

Caira, Crystalline Polymorphism of Organic Compounds, Topics in Current Chemistry, vol. 198, 1998, pp. 163-208.
Henck Jan-Olav, Polymorphie von Arzneistoffen Eine wirtschaftliche Herausforderung, Jan. 1, 1997, Pharmind, Ind. 59, Nr. 2, pp. 165-169.
European Patent N. 1 698630, Opposition Proceedings, "Notice of opposition to the European Patent", Jun. 3, 2015.
Braga D et al., The Structure-Property Relationship of Four Crystal Forms of Rifaximin, Aug. 9, 2012, CrystEngComm, 14, pp. 6404-6411.
Physicians' Desk Reference, Mar. 10, 2007, 2790-2791, 62, Thomson Healthcare, Montvale XP002601190.
Dissolution test for solid dosage forms, 2007, 266-275, European Pharmacopoeia Ed. 6.0.
Disintegration of tablets and capsules, 2008, 3943-3945, European Pharmacopoeia Ed. 6.3.
Annex to European Commission Directive 92/69/EEC, Official Journal of the European Communities, No L 383/113, 2 pages, 1992.
OECD Guidelines for Testing of Chemicals, 1995, 1-7.
Rifaximin, 2001, 1475, Merck Index XIII ed.
Rifamide, 2001, 1474, Merck Index XIII ed.
Resistant to crushing of tablets, 2011, 267, Chapter 2.9.8, European Pharmacopoeia Ed. 7.0.
Disintegration of suppositories and pessaries, 2011, 255-256, Chapter 2.9.2., European Pharmacopoeia Ed. 7.0.
Rifaximin, 2009, 4955-4957, European Pharmacopoeia 6.5.
Rifaximin, 2011, 3459-3460, European Pharmacopoeia 7.1.
Bass N.M. et al., Rifaximin treatment in hepatic encephalopathy, Mar. 25, 2010, 1071-1081, 362 (12), N. Engl. J. Med.
Prantera C. et al., Rifaximin and Crohn's disease., Nov. 14, 2013, 7487-7488, 19 (42), World J. Gastroenterol.
Scarpignato C. et al., Rifaximin, a poorly absorbed antibiotic: pharmacology and clinical potential., 2005, 36-66, 51 Suppl 1, Chemotherapy.
Stradi R. et al., Structural elucidation of the Rifaximin Ph. Eur. Impurity H., 2010, 858-865, 51 (4), J. Pharm. Biomed. Anal.
ICH Topic Q 6 A, Specifications: Test Procedures and Acceptance Criteria for New Drug Substances and New Drug Products: Chemical Substances, May 1, 2000, 1-32, European Medicines Agency.
Italian Product Label for NORMIX (rifaximin), Apr. 23, 1985, 1-6.
Guillemot D., Antibiotic use in humans and bacterial resistance., Jan. 10, 1999, 494-498, 2 (5), Curr. Opin. Microbiol.
Debbia E.A. et al., Effects of rifaximin on bacterial virulence mechanisms at supra- and sub-inhibitory concentrations., Apr. 1, 2008, 186-194, 20 (2), J. Chemother.
Jiang Z.D. et al., Rifaximin-induced alteration of virulence of diarrhoea-producing *Escherichia coli* and Shigella sonnei., Mar. 1, 2010, 278-281, 35 (3), Int. J. Antimicrob. Agents.
Kibbe A.H., Handbook of pharmaceutical Excipients., Jan. 15, 2000, 165, 442, American Pharm. Association and Pharm. Press.
Qing Li et al., Solvothermal growth of vaterite in the presence of ethylene glycol, 1,2-propanediol and glycerin., Mar. 1, 2002, 357-362, 236 (1-3), J. Crystal Growth.
Uresti et al., Effect of sugars and polyols on the functional and mechanical properties of pressure-treated arrowtooth flounder (*Atheresthes stomias*) proteins, Feb. 5, 2005, 964-973, Food Hydrocolloids 19.
Cruz-Cabeza et al, Conformational polymorphism, Dec. 18, 2013, 2170-2191, Chemical Reviews 114.
Guillory, Generation of polymorphism, hydrates, solvates, and amorphous solids, Jan. 1, 1999, 183-226.
Bauer et al., Ritonavir: an extraordinary example of conformational polymorphism, Mar. 10, 2001, 859-866, Pharmaceutical Research, vol. 18, No. 6.
Brittain, Polymorphism and solvatomorphism 2009, Nov. 24, 2010, 1260-1279, Journal of Pharmaceutical Sciences, vol. 100, No. 4.
Corti et al., Application of derivative resolution of UV spectra to the quality control of rifaximine and its possible impurities, Jan. 1, 1992, 76-79, Pharm. Acta Hel v. 67 n. 3.
Rossi et al., NMR studies of a new class of rifaximin-derived molecules: rifaximin OR (Open ring), Jan. 1, 1996, 268-269, J. Chem. Research (S).
Martini et al., Solution structure of rifaximin and its synthetic derivative rifaximin OR determined by experimental NMR and theoretical simulation methods., May 1, 2004, 2163-2172, Bioorganic & Medicinal Chemistry 12.
Swanepoel et al. Quality evaluation of generic drugs by dissolution test: changing the USP dissolution medium to distinguish between active and non-active mebendazole, May 1, 2003, 345-349, European Journal of Pharmaceutics and Biopharmaceutics 55.
Liu et al., Structure elucidation of two unknown oxydic degradation impurities of rifaximin, Jan. 1, 2011, 3251-3256, Asian Journal of Chemistry vol. 23, No. 7.
Agrawal et al., Solid-state characterization of rifampicin samples and its biopharmaceutic relevance., Jun. 1, 2004, 127-144, European Journal of Pharmaceutical Sciences 22.
Son et al., A new respirable form of rifampicin, Feb. 13, 2011, 366-376, European Journal of Pharmaceutics and Biopharmaceutics 78.
Blandizzi et al., Impact of crystal polymorphism on the systemic bioavailability of rifaximin, an antibiotic acting locally in the gastrointestinal tract, in healthy volunteers, Dec. 16, 2014, 1-11, Drug Design, Development and Therapy 9.
Saifee et al., Drug polymorphism: a review, Dec. 1, 2009, 291-306, International Journal of Health Research, 2(4).
Kremer et al., Re-emergence of tuberculosis: strategies and treatment., Feb. 1, 2002, 153-157, Expert Opin. Drugs 11(2).

(56) References Cited

OTHER PUBLICATIONS

Marchese et al., In vitro activity of rifaximin, metronidazole and vancomycin against Clostridium difficile and the rate of selection of spontaneously resistant mutant, Jul. 1, 2000, 253-266, Chemotherapy 45.
Non-Final Office Action issued by the US Patent and Trademark Office on Apr. 17, 2007 in U.S. Appl. No. 11/135,651. 6 pages.
Abandonment issued by the US Patent and Trademark Office on Oct. 25, 2007 in U.S. Appl. No. 11/135,651. 2 pages.
Examination support document filed on Jun. 4, 2009 by Applicant in U.S. Appl. No. 12/478,638. 6 pages.
Examiner Interview Summary on Aug. 18, 2009 for U.S. Appl. No. 12/478,638. 2 pages.
Declaration of Inventor submitted to the US Patent and Trademark Office on Mar. 9, 2009 in U.S. Appl. No. 12/478,638. 11 pages.
Notice of Abandonment submitted Nov. 29, 2012 in U.S. Appl. No. 13/448,356. 2 pages.
Non-Final Office Action issued by the US Patent and Trademark Office on Aug. 1, 2013 in U.S. Appl. No. 13/680,967. 6 pages.
Response to Non-Final Office Action submitted Jan. 31, 2014 in U.S. Appl. No. 13/680,967. 12 pages.
Final Office Action issued by the US Patent and Trademark Office on Feb. 10, 2014 in U.S. Appl. No. 13/680,967. 6 pages.
Non-Final Office Action issued by the US Patent and Trademark Office on Jul. 12, 2012 in U.S. Appl. No. 13/463,714. 6 pages.
Notice of Abandonment Dec. 8, 2013 in U.S. Appl. No. 13/463,714. 2 pages.
Examiner Interview Summary issued by the US Patent and Trademark Office on Feb. 24, 2010 in U.S. Appl. No. 11/873,841. 3 pages.
Request for continued Examination submitted Oct. 27, 2010 in U.S. Appl. No. 13/873,841 3 pages.
Response to Non-Final Rejection submitted Jul. 20, 2012 in U.S. Appl. No. 13/041,348 4 pages.
Final Rejection issued by the US Patent and Trademark Office on Aug. 6, 2012 in U.S. Appl. No. 13/041,348. 5 pages.
Response to Final Rejection submitted Nov. 2, 2010 in U.S. Appl. No. 13/041,348. 8 pages.
Request for continued Examination submitted Nov. 2, 2012 in U.S. Appl. No. 13/0441,348 1 page.
Terminal disclaimer submitted Nov. 2, 2012 in U.S. Appl. No. 13/041,348. 2 pages.
Terminal disclaimer submitted Oct. 23, 2009 in U.S. Appl. No. 12/119,600. 2 pages.
Request for Continued Examination submitted Feb. 16, 2010 in U.S. Appl. No. 12/119,600. 3 pages.
Examiner Interview Summary issued by the US Patent and Trademark Office on Feb. 26, 2010 in U.S. Appl. No. 12/119,600. 3 pages.
Non-Final Rejection issued by the US Patent and Trademark Office on May 10, 2010 in U.S. Appl. No. 12/119,600. 5 pages.
Non-Final Rejection issued by the US Patent and Trademark Office on Apr. 30, 2010 in U.S. Appl. No. 12/119,612. 4 pages.
Terminal disclaimer submitted Oct. 29, 2010 U.S. Appl. No. 12/119,612. 2 pages.
Response to Non-Final Rejection submitted Oct. 29, 2010 in U.S. Appl. No. 12/119,612. 12 pages.
Request for Continued Examination submitted Jan. 26, 2011 in U.S. Appl. No. 12/119,612. 3 pages.
Notice of Allowance submitted Mar. 3, 2011 in U.S. Appl. No. 12/119,612. 3 pages.
Terminal disclaimer submitted Dec. 20, 2011 in U.S. Appl. No. 13/041,347. 4 pages.
Non-Final Rejection issued by the US Patent and Trademark Office on Aug. 1, 2013 in U.S. Appl. No. 13/679,602. 6 pages.
Response to Non-Final Rejection submitted Jan. 31, 2014 in U.S. Appl. No. 13/679,602. 9 pages.
Final Rejection issued by the US Patent and Trademark Office on Feb. 10, 2014 in U.S. Appl. No. 13/679,602. 6 pages.
Non-Final Office Action issued by the US Patent and Trademark Office on May 28, 2010 in U.S. Appl. No. 12/119,630. 4 pages.
Non-Final Office Action issued by the US Patent and Trademark Office on Apr. 15, 2011 in U.S. Appl. No. 12/955,607. 3 pages.
Examiner Interview Summary issued by the US Patent and Trademark Office on Jun. 13, 2011 in U.S. Appl. No. 12/955,607. 3 pages.
International Search Report issued on Jul. 28, 2005 for the International Patent Application N. PCT/EP2004/012490. 4 pages.
International Preliminary Report on Patentability issued on May 8, 2006 for the application N. PCT/EP2004/012490. 6 pages.
Communication from European Examination Division issued on Nov. 29, 2006 for the application n. EP04797615.4. 2 pages.
Communication from European Examination Division after Further Processing Nov. 29, 2006 for the application n. EP 04797615.4.
Communication filed by Applicant in response to European Examination Division Mar. 12, 2010 for theapplication n. 04797615.4. 9 pages.
Written submission filed by the Applicant on Nov. 21, 2013, in preparation of Oral Proceeding for the European application n. 04797615.4. 5 pages.
Written submission filed by the Applicant on Jan. 22, 2014 in preparation of Oral Proceeding for the application EP 04797615.4. 2 pages.
Search Opinion and Search Report issued by the European Patent Office on Jun. 21, 2010 for the European Patent Application N. 10004589. 5 pages.
Amendments before examination of the European Patent Office submitted on Oct. 5, 2010 for the application No. 10004589.7. 15 pages.
The Communication issued by European Examination Division on Aug. 1, 2013 for the Application No. 10004589.7. 4 pages.
European Search Opinion and Search Report issued by the European Patent Office on Jun. 1, 2010 for the application No. 10004590.5. 4 pages.
Response filed by the Applicant on Sep. 10, 2010 to the Examination Division for the Application No. 1004590.5 13 pages.
Issued on Sep. 1, 2013 by the European Examination Division for the application No. 100004590.5 3 pages.
Response to Final Rejection submitted May 7, 2014 in U.S. Appl. No. 13/680,967 3 pages.
Response to Final Rejection submitted May 6, 2014 in U.S. Appl. No. 13/679,602 3 pages.
European Search Opinion and Search Report issued by the European Patent Office on Jun. 24, 2010 for the application No. 10004589.7. 5 pages.
European patent application No. 10004589.7 on Sep. 5, 2014. 2 pages.
Amendments before examination of the European Patent Office submitted on Sep. 10, 2010 for the application No. 10004590.5. 13 pages.
Official Communication issued by the European Patent Office on Aug. 1, 2010 for the application No. 10004590.5. 3 pages.
Closing of European patent application No. 10004590.5 on Aug. 29, 2014. 2 pages.
Non-Final Office Action issued by the US Patent and Trademark Office on May 6, 2015 in U.S. Appl. No. 14/457,909. 24 pages.
Non-Final Office Action issued by the US Patent and Trademark Office on May 7, 2015 in U.S. Appl. No. 14/458,197. 24 pages.
Non-Final Rejection issued by the US Patent and Trademark Office on Sep. 19, 2005 in U.S. Appl. No. 10/728,090. 5 pages.
Response to Non-Final Rejection submitted Jan. 17, 2006 in U.S. Appl. No. 10/728,090 17 pages.
Restriction Requirement issued by the US Patent and Trademark Office on Jul. 16, 2013 in U.S. Appl. No. 13/582,676. 7 pages.
Response to Restriction Requirement submitted Oct. 10, 2013 in U.S. Appl. No. 13/582,676 6 pages.
European Search Opinion and European Search Report issued Jun. 6, 2006 for the European Patent application 06004219.9. 4 pages.
Amendment filed before European Patent Office before examination, Jul. 6, 2006 for the European Patent Application 06004219.9. 5 pages.
European Search opinion and Search Report issued by the European Patent Office on Jun. 6, 2006 for the application No. 06004220.7. 3 pages.

(56) References Cited

OTHER PUBLICATIONS

Amendment filed before European Patent Office before examination, Jul. 6, 2006 for the European Patent Application 06004220.7. 5 pages.
Written Opinion issued on Nov. 15, 2011, by International Searching Authorities for the International application PCT/IB2011/050933. 7 pages.
International Search Report issued on Nov. 16, 2011, for the International application PCT/IB2011/050933 3 pages.
Written Opinion issued on Apr. 16, 2012 by IPEA for the International application PCT/IB2011/050933 7 pages.
Response filed on May 7, 2012 to International Preliminary Examination Authorities for the International application PCT/IB2011/050933. 4 pages.
International Preliminary Report on Patentability issued on Jun. 25, 2012, by the EPO for the International application PCT/IB2011/050933. 12 pages.
European Search Report issued by the European Patent Office on Jul. 14, 2004 for the application No. 04005541.0 5 pages.
Official Communication issued by the European Patent Office on Feb. 16, 2006 for the application No. 04005541.0 3 pages.
Reply to Official Communication issued by the European Patent Office submitted on May 3, 2006 for the application No. 04005541.0. 14 pages.
Official Communication issued by the European Patent Office on May 15, 2006 for the application No. 04005541.0 2 pages.
Reply to Official Communication issued by the European Patent Office submitted on Jun. 12, 2006 for the application No. 0405541.0. 2 pages.
Communication about the intention to grant issued by the European Patent Office on Feb. 1, 2007 for the application No. 04005541.0. 4 pages.
Communication about the intention to grant issued by the European Patent Office on Oct. 29, 2007 for the application No. 06004220.7. 4 pages.
Communication about the intention to grant issued by the European Patent Office on Oct. 29, 2007 for the application No. 06004219.9. 4 pages.
Affidavit Viscomi submitted Jan. 17, 2006 in U.S. Appl. No. 10/728,090. 12 pages.
Reply to Official Communication issued by the European Patent Office submitted on Jun. 12, 2006 for the application No. 04005541.0. 2 pages.
Request for Continued Examination submitted Jan. 19, 2010 in U.S. Appl. No. 11/658,702 3 pages.
Request for Certificate of Correction submitted Jun. 28, 2012 in U.S. Appl. No. 11/658,702. 9 pages.
Examiner Interview Summary issued Feb. 25, 2010 by the US Patent and Trademark Office in U.S. Appl No. 11/658,702. 3 pages.
Examiner Initiated Interview Summary on Apr. 27, 2012 in U.S. Appl. No. 11/658,702 6 pages.
Certificate of Correction issued by the US Patent and Trademark Office on Jul. 31, 2012 in U.S. Appl. No. 11/658,702. 6 pages.
Applicant Initiated Interview Summary on Jan. 30, 2012 in U.S. Appl. No. 11/658,702 7 pages.
Amendment submitted Jan. 19, 2011 with filing of CPA/RCE in U.S. Appl. No. 11/658,702 7 pages.
Amendment and Response after Allowance submitted Dec. 11, 2009 in U.S. Appl. No. 11/658,702. 7 pages.
Terminal disclaimer submitted Apr. 18, 2013 in U.S. Appl. No. 13/488,345. 2 pages.
Response to Non-Final Rejection submitted Nov. 7, 2012 in U.S. Appl. No. 13/488,345 8 pages.
Response to Final Rejection submitted Apr. 18, 2013 in U.S. Appl. No. 13/488,345. 8 pages.
Non-Final Rejection issued by the US Patent and Trademark Office on Aug. 7, 2012 in U.S. Appl. No. 13/488,345. 5 pages.
Final Rejection issued by the US Patent and Trademark Office on Dec. 18, 2012 in U.S. Appl. No. 13/488,345. 5 pages.
Terminal disclaimer submitted Nov. 27, 2013 in U.S. Appl. No. 13/950,642. 1 page.
Response to Non-Final Rejection submitted Nov. 27, 2013 in U.S. Appl. No. 13/950,642 10 pages.
Non-Final Rejection issued on Sep. 9, 2013 by the US Patent and Trademark Office in U.S. Appl. No. 13/950,642. 5 pages.
International Search Report and Written Opinion dated Jul. 29, 2006 as issued in PCT/EP2006/001755 10 pages.
International Preliminary Report on Patentability dated May 8, 2007 as issued in PCT/EP2006/001755. 5 pages.
Extended European Search Report dated Aug. 3, 2005 as issued in EP05004695.2. 7 pages.
Communication issued by the Examining Division of the European Patent Office on Oct. 9, 2007 in EP05004695.2. 4 pages.
Communication issued by the Examining Division of the European Patent Office on Jul. 31, 2013 in EP05004695.2. 6 pages.
Communication issued by the Examining Division of the European Patent Office on May 7, 2009 in EP05004695.2. 4 pages.
Communication issued by the Examining Division of the European Patent Office on Jan. 19, 2011 in EP05004695.2. 6 pages.
Reply to Official Communication issued by the European Patent Office submitted on Feb. 19, 2008 for the application n. 05004695.2. 6 pages.
Reply to Official Communication issued by the European Patent Office submitted on Sep. 1, 2009 for the application n. 05004695.2. 15 pages.
Reply to Official Communication issued by the European Patent Office submitted on May 23, 2011 for the application n. 05004695.2. 10 pages.
Reply to Official Communication issued by the European Patent Office submitted on Nov. 13, 2013 for the application n. 05004695.2. 13 pages.
Communication about the intention to grant issued by the European Patent Office on May 22, 2014 for the application n. 05004695.2. 5 pages.

POLYMORPHOUS FORMS OF RIFAXIMIN, PROCESSES FOR THEIR PRODUCTION AND USE THEREOF IN THE MEDICINAL PREPARATIONS

RELATED APPLICATIONS

The present application is a continuation of U.S. patent application Ser. No. 13/950,642 filed Jul. 25, 2013, which a continuation under 35 U.S.C. §120 of U.S. patent application Ser. No. 13/488,345, filed Jun. 4, 2012,now U.S. Pat. No. 8,518,949, issued on Aug. 4, 2013, which is a continuation of U.S. patent application Ser. No. 11/658,702, filed Oct. 8, 2007, now U.S. Pat. No. 8,193,196, issued on Jun. 5, 2012, which in turn is filed under 35 U.S.C. §371 as the U.S. national application of International patent application No. PCT/EP2006/001755, filed Feb. 27, 2006, which in turn claims priority to the European Patent Application No. EP 05004695.2, filed Mar. 3, 2005, the entire disclosure of all of which is hereby incorporated by reference herein, including the drawings.

BACKGROUND OF THE INVENTION

The rifaximin (INN; see The Merck Index, XIII Ed., 8304) is an antibiotic pertaining to the rifamycin class, exactly it is a pyrido-imidazo rifamycin described and claimed in the Italian Patent IT 1154655, while the European Patent EP 0161534 describes and claims a process for its production starting from the rifamycin O (The Merck Index, XIII Ed., 8301).

Both these patents describe the purification of the rifaximin in a generic way saying that the crystallization can be carried out in suitable solvents or solvent systems and summarily showing in some examples that the product coming from the reaction can be crystallized from the 7:3 mixture of ethyl alcohol/water and can be dried both under atmospheric pressure and under vacuum without saying in any way neither the experimental conditions of crystallization and drying, nor any distinctive crystallographic characteristic of the obtained product.

The presence of different polymorphs had not been just noticed and therefore the experimental conditions described in both patents had been developed with the goal to get a homogeneous product having a suitable purity from the chemical point of view, apart from the crystallographic aspects of the product itself.

It has now be found, unexpectedly, that some polymorphous forms exist whose formation, in addition to the solvent, depends on the conditions of time and temperature at which both the crystallization and the drying are carried out.

These orderly polymorphous forms will be, later on, conventionally identified as rifaximin δ (FIG. 1) and rifaximin ε (FIG. 2) on the basis of their respective specific diffractograms reported in the present application.

The polymorphous forms of the rifaximin have been characterized through the technique of the powder X-ray diffraction.

The identification and characterization of these polymorphous forms and, contemporarily, the definition of the experimental conditions for obtaining them is very important for a compound endowed with pharmacological activity which, like the rifaximin, is marketed as medicinal preparation, both for human and veterinary use. In fact it is known that the polymorphism of a compound that can be used as active principle contained in a medicinal preparation can influence the pharmaco-toxicologic properties of the drug. Different polymorphous forms of an active principle administered as drug under oral or topical form can modify many properties thereof like bioavailability, solubility, stability, color, compressibility, flowability and workability with consequent modification of the profiles of toxicological safety, clinical effectiveness and productive efficiency.

What above mentioned is confirmed with authority by the fact that the authorities that regulate the grant of the authorization for the admission of the drugs on the market require that the manufacturing methods of the active principles are standardized and controlled in such a way that they give homogeneous and sound results in terms of polymorphism of the production batches (CPMP/QWP/96, 2003—Note for Guidance on Chemistry of new Active Substance; CPMP/ICH/367/96—Note for guidance specifications: test procedures and acceptance criteria for new drug substances and new drug products: chemical substances; Date for coming into operation: May 2000).

The need of the above-mentioned standardization has further been strengthened just in the field of the rifamycin antibiotics from Henwood S. Q., de Villiers M. M., Liebenberg W. and Lotter A. P., Drug Development and Industrial Pharmacy, 26 (4), 403-408, (2000), who have ascertained that different production batches of the rifampicin (INN) made from different manufacturers differ among them because they show different polymorphous characteristics, and as a consequence they show different profiles of dissolution together with consequent alteration of the respective pharmacological properties.

By applying the processes of crystallization and drying generically disclosed in the previous patents IT 1154655 and EP 0161534 it has been found that under some experimental conditions the poorly crystalline form of the rifaximin is obtained while under other experimental conditions the other crystalline polymorphous forms of the rifaximin are obtained. Moreover it has been found that some parameters, absolutely not disclosed in the above-mentioned patents, like for instance the conditions of preservation and the relative humidity of the ambient, have the surprising effect to determine the form of the polymorph.

The polymorphous forms of the rifaximin object of the present patent application were never seen or hypothesized, while thinking that a sole homogeneous product would always have been obtained whichever method would have been chosen within the range of the described conditions, irrespective of the conditions used for crystallizing, drying and preserving.

It has now been found that the formation of the δ and ε forms depends on the presence of water within the crystallization solvent, on the temperature at which the product is crystallized and on the amount of water present into the product at the end of the drying phase.

The form δ and the form ε of the rifaximin have then been synthesized and they are the object of the invention.

In particular the form δ is characterized by the residual content of water in the dried solid material in the range from 2.5% and 6% (w/w), more preferably from 3% and 4.5%, while the form ε is the result of a polymorphic transition under controlled temperature moving from the form δ.

These results have a remarkable importance as they determine the conditions of industrial manufacturing of some steps of working which could not be considered critical for the determination of the polymorphism of a product, like for instance the maintaining to a crystallized product a quantity of water in a stringent range of values, or the process of drying the final product, in which a form, namely form δ, has to be obtained prior to continuing the drying to obtain the form δ, or the conditions of preservation of the end product, or the characteristics of the container in which the product is preserved.

Rifaximin exerts its broad antibacterial activity in the gastrointestinal tract against localized gastrointestinal bacteria that cause infectious diarrhea including anaerobic strains. It has been reported that rifaximin is characterized by a negligible systemic absorption, due to its chemical and physical characteristics (Descombe J. J. et al. Pharmacokinetic study of rifaximin after oral administration in healthy volunteers. Int J Clin. Pharmacol. Res., 14 (2), 51-56, (1994))

Now we have found that it is possible on the basis of the two identified polymorphic forms of rifaximin to modulate its level of systemic adsorption, and this is part of the present invention, by administering distinct polymorphous forms of rifaximin, namely rifaximin δ and rifaximin ε. It is possible to have a difference in the adsorption of almost 100 folds in the range from 0.001 to 0.3 μg/ml in blood.

The evidenced difference in the bioavailability is important because it can differentiate the pharmacological and toxicological behavior of the two polymorphous of rifaximins δ and ε.

As a matter of fact, rifaximin ε is negligibly absorbed through the oral route while rifaximin δ shows a mild absorption.

Rifaximin ε is practically not absorbed, might act only through a topical action, including the case of the gastrointestinal tract, with the advantage of very low toxicity.

On the other way, rifaximin δ, which is mildly absorbed, can find an advantageous use against systemic microorganisms, able to hide themselves and to partially elude the action of the topic antibiotics.

In respect of possible adverse events coupled to the therapeutic use of rifaximin of particular relevance is the induction of bacterial resistance to the antibiotics. Generally speaking, it is always possible in the therapeutic practice with antibiotics to induce bacterial resistance to the same or to other antibiotic through selection of resistant strains.

In case of rifaximin, this aspect is particularly relevant, since rifaximin belongs to the rifamycin family, a member of which, the rifampicin, is largely used in tuberculosis therapy. The current short course treatment of tuberculosis is a combination therapy involving four active pharmaceutical ingredients: rifampicin, isoniazid, ethambutol and pyrazinamide and among them rifampicin plays a pivotal role. Therefore, any drug which jeopardized the efficacy of the therapy by selecting for resistance to rifampicin would be harmful. (Kremer L. et al. "Re-emergence of tuberculosis: strategies and treatment", Expert Opin. Investig. Drugs, 11 (2), 153-157, (2002)).

In principle, looking at the structural similarity between rifaximin and rifampicin, it might be possible by using rifaximin to select resistant strains of *M. tuberculosis* and to induce cross-resistance to rifampicin. In order to avoid this negative event it is crucial to have a control of quantity of rifaximin systemically absorbed.

Under this point of view, the difference found in the systemic absorption of the δ and ε forms of the rifaximin is significant, since also at sub-inhibitory concentration of rifaximin, such as in the range of from 0.1 to 1 μg/ml, selection of resistant mutants has been demonstrated to be possible (Marchese A. et al. In vitro activity of rifaximin, metronidazole and vancomycin against *clostridium difficile* and the rate of selection of spontaneously resistant mutants against representative anaerobic and aerobic bacteria, including ammonia-producing species. Chemotherapy, 46(4), 253-266, (2000)).

According to what above said, the importance of the present invention, which has led to the knowledge of the existence of the above mentioned rifaximin polymorphous forms and to various industrial routes for manufacturing pure single forms having different pharmacological properties, is clearly strengthened.

The above-mentioned δ and ε forms can be advantageously used as pure and homogeneous products in the manufacture of medicinal preparations containing rifaximin.

As already said, the process for manufacturing rifaximin from rifamycin O disclosed and claimed in EP 0161534 is deficient from the point of view of the purification and identification of the product obtained; it shows some limits also from the synthetic point of view as regards, for instance, the very long reaction times, from 16 to 72 hours, very little suitable for an industrial use and moreover because it does not provide for the in situ reduction of the rifaximin oxidized that may be formed within the reaction mixture.

Therefore, a further object of the present invention is an improved process for the industrial manufacturing of the δ and ε forms of the rifaximin, herein claimed as products and usable as defined and homogeneous active principles in the manufacture of the medicinal preparations containing such active principle.

DESCRIPTION OF THE INVENTION

Figure 1:
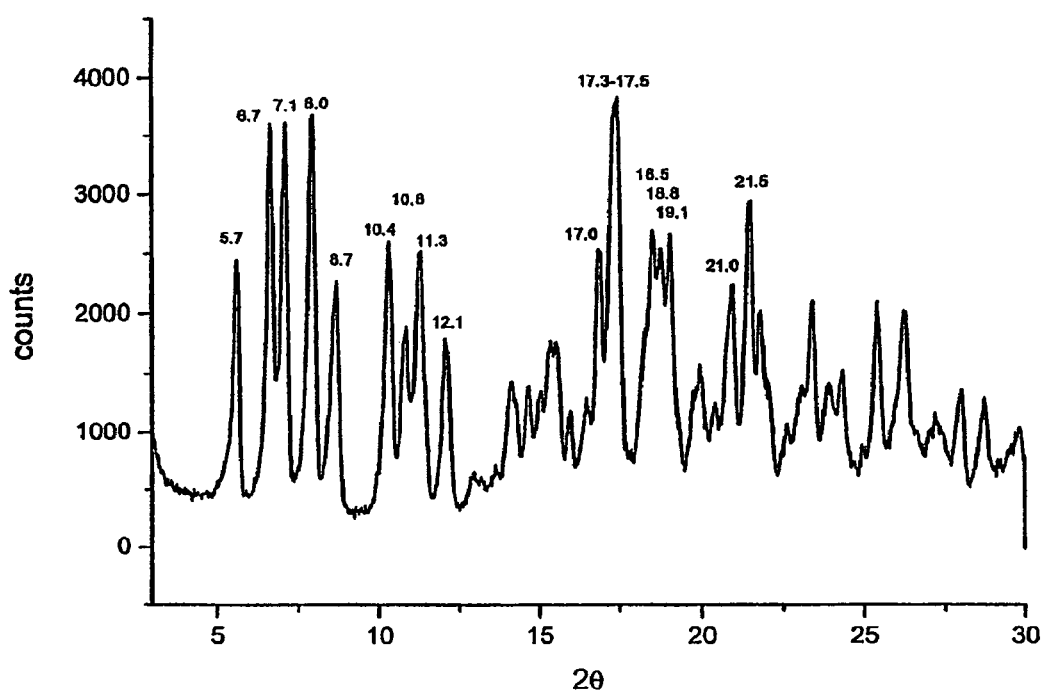
FIG. 1 is a powder X-ray diffractogram of rifaximin δ.

As already said, the form δ and the form ε of the antibiotic known as rifaximin (INN), processes for their production and the use thereof in the manufacture of medicinal preparations for oral or topical route, are object of the present invention.

A process object of the present invention comprises reacting one molar equivalent of rifamycin O with an excess of 2-amino-4-methylpyridine, preferably from 2.0 to 3.5 molar equivalents, in a solvent mixture made of water and ethyl alcohol in volumetric ratios between 1:1 and 2:1, for a period of time between 2 and 8 hours at a temperature between 40° C. and 60° C.

At the end of the reaction the reaction mass is cooled to room temperature and is added with a solution of ascorbic acid in a mixture of water, ethyl alcohol and aqueous concentrated hydrochloric acid, under strong stirring, in order to reduce the small amount of oxidized rifaximin that forms during the reaction and finally the pH is brought to about 2.0 by means of a further addition of concentrated aqueous solution of hydrochloric acid, in order to better remove the excess of 2-amino-4-methylpyridine used in the reaction. The suspension is filtered and the obtained solid is washed with the same solvent mixture water/ethyl alcohol used in the reaction. Such semi finished product is called "raw rifaximin".

The raw rifaximin can be directly submitted to the subsequent step of purification. Alternately, in case long times of preservation of the semi finished product are expected, the raw rifaximin can be dried under vacuum at a temperature lower than 65° C. for a period of time between 6 and 24 hours, such semi finished product is called "dried raw rifaximin".

The so obtained raw rifaximin and/or dried raw rifaximin are purified by dissolving them in ethyl alcohol at a temperature between 45° C. and 65° C. and by crystallizing them by addition of water, preferably in weight amounts between 15% and 70% in respect of the amount by weight of the ethyl alcohol used for the dissolution, and by keeping the obtained suspension at a temperature between 50° C. and 0° C. under stifling during a period of time between 4 and 36 hours.

The suspension is filtered and the obtained solid is washed with water and dried under vacuum or under normal pressure, with or without a drying agent, at a temperature between the room temperature and 105° C. for a period of time between 2 and 72 hours.

The achievement of the δ and ε forms depends on the conditions chosen for the crystallization. In particular, the composition of the solvent mixture from which the crystallization is carried out, the temperature at which the reaction mixture is kept after the crystallization and the period of time at which that temperature is kept, have proven to be critical.

More precisely, the δ and ε rifaximins are obtained when the temperature is first brought to a value between 28° C. and 32° C. in order to cause the beginning of the crystallization, then the suspension is brought to a temperature between 40° C. and 50° C. and kept at this value for a period of time between 6 and 24 hours, then the suspension is quickly cooled to 0° C., in a period of time between 15 minutes and one hour, is filtered, the solid is washed with water and then is dried.

The step of drying has an important part in obtaining the δ and ε polymorphous forms of the rifaximin and has to be checked by means of a suitable method fit for the water dosage, like for instance the Karl Fisher method, in order to check the amount of remaining water present in the product under drying.

The obtaining of the rifaximin δ during the drying in fact depends on the end remaining amount of water which should be comprised from 2.5% (w/w) and 6% (w/w), more preferably between—3% and 4.5%, and not from the experimental conditions of pressure and temperature at which this critical limit of water percent is achieved.

In order to obtain the poorly adsorbed ε form it has to start from the δ form and it has to be continued the drying under vacuum or at atmospheric pressure, at room temperature or at high temperatures, in the presence or in the absence of drying agents, provided that the drying is prolonged for the time necessary so that the conversion in form E is achieved.

Both the forms δ and ε of the rifaximin are hygroscopic, they absorb water in a reversible way during the time in the presence of suitable conditions of pressure and humidity in the ambient and are susceptible of transformation to other forms.

The transitions from one form to another result to be very important in the ambit of the invention, because they can be an alternative manufacturing method for obtaining the form desired for the production of the medicinal preparations. Therefore, the process that allows to turn the rifaximin δ into rifaximin ε in a valid industrial manner is important part of the invention.

The process concerning the transformation of the rifaximin δ into rifaximin ε comprises drying the rifaximin δ under vacuum or at atmospheric pressure, at room temperature or at high temperatures, in the presence or in the absence of drying agents, and keeping it for a period of time until the conversion is obtained, usually between 6 and 36 hours.

From what above said, it results that during the phase of preservation of the product a particular care has to be taken so that the ambient conditions do not change the water content of the product, by preserving the product in ambient having controlled humidity or in closed containers that do not allow in a significant way the exchange of water with the exterior ambient.

Figure 2:
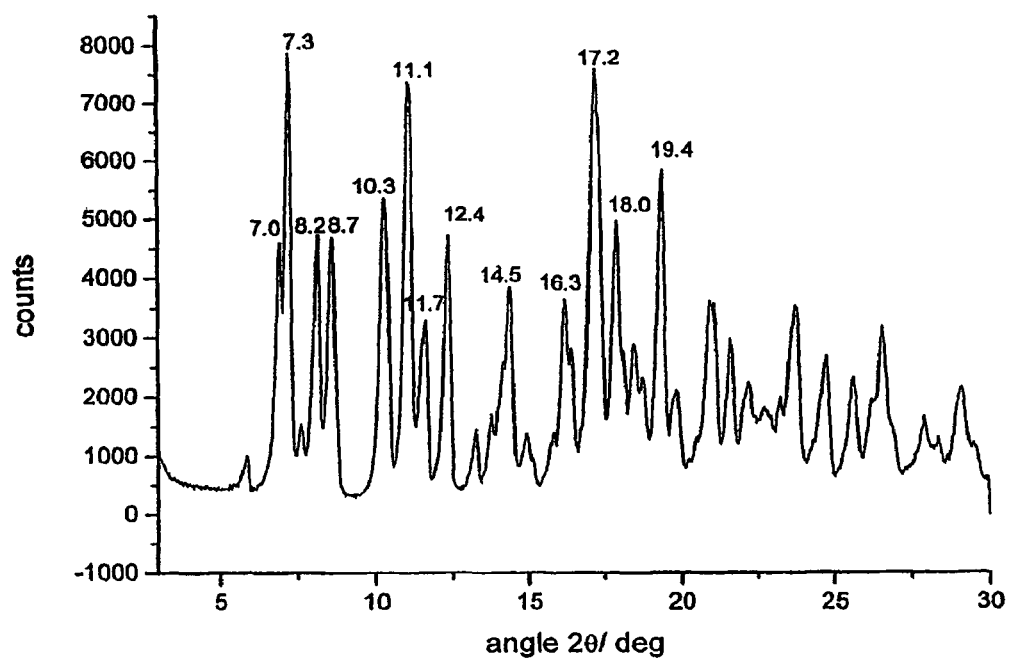
FIG. 2 is a powder X-ray diffractogram of rifaximin ε.

The polymorph called rifaximin δ is characterized from a content of water in the range between 2.5% and 6%, preferably between 3.0% and 4.5% and from a powder X-ray diffractogram (reported in FIG. 1) which shows peaks at the values of the diffraction angles 2θ of 5.70°±0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2, 21.5°±0.2. The polymorph called rifaximin E is characterized from a powder X-ray diffractogram (reported in FIG. 2) which shows peaks at the values of the diffraction angles 2θ of 7.0°±0.2, 7.3°±0.2, 8.2°±0.2, 8.7°±0.2, 10.3°±0.2, 11.1°±0.2, 11.7°±0.2, 12.4°±0.2, 14.5°±0.2, 16.3°±0.2, 17.2°±0.2, 18.0°±0.2, 19.4°±0.2.

The diffractograms have been carried out by means of the Philips X'Pert instrument endowed with Bragg-Brentano geometry and under the following working conditions:

X-ray tube: Copper
Radiation used: K (α1), K (α2)
Tension and current of the generator: KV 40, mA 40
Monochromator: Graphite
Step size: 0.02
Time per step: 1.25 seconds
Starting and final angular 2θ value: 3.0°/30.0°

The evaluation of the content of water present in the analysed samples has always been carried out by means of the Karl Fisher method.

Rifaximin δ and rifaximin ε differ each from other also because they show significant differences as regards bioavailability.

A bioavailability study of the two polymorphs has been carried out on Beagle female dogs, treated them by oral route with a dose of 100 mg/kg in capsule of one of the polymorphs, collecting blood samples from the jugular vein of each animal before each dosing and 1, 2, 4, 6, 8 and 24 hours after each dosing, transferring the samples into tubes containing heparin and separating the plasma by centrifugation.

The plasma has been assayed for rifaximin on the validated LC-MS/MS method and the maximum observed plasma concentration (Cmax), the time to reach the Cmax (Tmax), and the area under the concentration-time curve (AUC) have been calculated.

The experimental data reported in the following table 1 clearly show that rifaximin ε is negligibly absorbed, while rifaximin δ is absorbed at a value (Cmax=0.308 μg/ml) comprised in the range of from 0.1 to 1.0 μg/ml.

TABLE 1

Pharmacokinetic parameters for rifaximin polymorphs following single oral administration of 100 mg/kg by capsules to female dogs

| | Cmax ng/ml Mean | Tmax h Mean | AUC0-24 ng · h/ml Mean |
|---|---|---|---|
| Polymorph δ | 308.31 | 2 | 801 |
| Polymorph ε | 6.86 | 4 | 42 |

The above experimental results further point out the differences existing among the two rifaximin polymorphs.

The forms δ and ε can be advantageously used in the production of medicinal preparations having antibiotic activity, containing rifaximin, for both oral and topical use. The medicinal preparations for oral use contain the rifaximin δ and ε together with the usual excipients as diluting agents like mannitol, lactose and sorbitol; binding agents like starches, gelatins, sugars, cellulose derivatives, natural gums and polyvinylpyrrolidone; lubricating agents like talc, stearates, hydrogenated vegetable oils, polyethylenglycol and colloidal silicon dioxide; disintegrating agents like starches, celluloses, alginates, gums and reticulated polymers; coloring, flavoring and sweetening agents.

All the solid preparations administrable by oral route can be used in the ambit of the present invention, for instance coated and uncoated tablets, capsules made of soft and hard gelatin, sugar-coated pills, lozenges, wafer sheets, pellets and powders in sealed packets.

The medicinal preparations for topical use contain the rifaximin δ and ε together with the usual excipients like white petrolatum, white wax, lanoline and derivatives thereof, stearylic alcohol, propylenglycol, sodium lauryl sulfate, ethers of the fatty polyoxyethylene alcohols, esters of the fatty polyoxyethylene acids, sorbitan monostearate, glyceryl monostearate, propylene glycol monostearate, polyethylene glycols, methylcellulose, hydroxymethylpropylcellulose, sodium carboxymethylcellulose, colloidal aluminum and magnesium silicate, sodium alginate.

All the topical preparations can be used in the ambit of the present invention, for instance the ointments, the pomades, the creams, the gels and the lotions.

The invention is herein below illustrated from some examples that do not have to be taken as a limitation of the invention: from what described results in fact evident that the forms δ and ε can be obtained by suitably combining between them the above mentioned conditions of crystallization and drying.

EXAMPLE 1

Preparation of Raw Rifaximin and of Dried Raw Rifaximin

In a three-necked flask equipped with mechanic stirrer, thermometer and reflux condenser, 120 ml of demineralized water, 96 ml of ethyl alcohol, 63.5 g of rifamycin O and 27.2 g of 2-amino-4-methylpyridine are loaded in succession at room temperature. After the loading, the mass is heated at 47±3° C., is kept under stirring at this temperature for 5 hours, then is cooled to 20±3° C. and, during 30 minutes, is added with a mixture, prepared separately, made of 9 ml of demineralized water, 12.6 ml of ethyl alcohol, 1.68 g of ascorbic acid and 9.28 g of aqueous concentrated hydrochloric acid. At the end of the addition, the mass is kept under stirring for 30 minutes at an interior temperature of 20±3° C. and then, at the same temperature, 7.72 g of concentrated hydrochloric acid are dripped until a pH equal to 2.0.

At the end of the addition, the mass is kept under stifling, always at an interior temperature equal to 20° C., for 30 minutes, then the precipitate is filtered and washed by means of a mixture made of 32 ml of demineralized water and of 25 ml of ethyl alcohol. The so obtained "raw rifaximin" (89.2 g) is dried under vacuum at room temperature for 12 hours obtaining 64.4 g of "dried raw rifaximin" which shows a water content equal to 5.6%. The product by further drying under vacuum until the weight of 62.2 g of dried raw rifaximin having a water content equal to 3.3%, whose diffractogram corresponds to the polymorphous form δ characterized from a powder X-ray diffractogram showing peaks at values of angles 2θ of 5.7°±0.2, 6.7°±0.2, 7.1°±0.2, 8.0°±0.2, 8.7°±0.2, 10.4°±0.2, 10.8°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2, 21.5°±0.2. The product is hygroscopic.

EXAMPLE 2

Preparation of Rifaximin ε

Example 1 is repeated and after having obtained the δ form, the solid powder is further dried under vacuum for 24 hours at the temperature of 65° C. The product obtained is rifaximin ε characterized from a powder X-ray diffractogram showing peaks at values of angles 2θ of 7.0°±0.2, 7.3°±0.2, 8.2°±0.2, 8.7°±0.2, 10.3°±0.2, 11.1°±0.2, 11.7°±0.2, 12.4°±0.2, 14.5°±0.2, 16.3°±0.2, 17.2°±0.2, 18.0°±0.2, 19.4°±0.2.

EXAMPLE 3

Bioavailability in Dogs by Oral Route

Eight pure-bred Beagle females dogs having 20 weeks of age and weighing between 5.0 and 7.5 kg have been divided into two groups of four.

The first of these group has been treated with rifaximin δ, the second with rifaximin ε according to the following procedure.

To each dog have been administered by the oral route 100 mg/kg of one of the rifaximin polymorphs into gelatin capsules and blood samples of 2 ml each have been collected from the jugular vein of each animal before each dispensing and 1, 2, 4, 6, 8 and 24 hours after the administration.

Each sample has been transferred into a tube containing heparin as anticoagulant and has been centrifuged; the plasma has been divided into two aliquots, each of 500 μl and has been frozen at −20° C.

The rifaximin contained in the plasma has been assayed by means of the validated LC-MS/MS method and the following parameters have been calculated according to standard non-compartmental analysis:

Cmax=maximum observed plasma concentration of rifaximin in the plasma;

Tmax=time at which the Cmax is reached;

AUC=area under the concentration-time curve calculated through the linear trapezoidal rule.

The results reported in the table 1 clearly show how the rifaximin δ is much more absorbed, more than 40 times, in respect of rifaximin ε, which is practically not absorbed.

What is claimed is:

1. A pharmaceutical composition comprising a therapeutically effective amount of rifaximin together with excipients, wherein the rifaximin has a X-ray powder diffraction pattern peaks at about 5.7°±0.2, 6.7°±0.2 and 8.0°±0.2.

2. The pharmaceutical composition of claim 1, wherein the X-ray powder diffraction pattern further comprises a peak at about 7.1°±0.2, 2θ.

3. The pharmaceutical composition of claim 1, wherein the X-ray powder diffraction pattern further comprises peaks at about 10.4°±0.2, 2θ.

4. The pharmaceutical composition of claim 1, wherein the X-ray powder diffraction pattern further comprises peaks at about 11.3°±0.2, 2θ.

5. The pharmaceutical composition of claim 1, wherein the X-ray powder diffraction pattern further comprises peaks at about 7.1°±0.2 and 10.8°±0.2, 2θ.

6. The pharmaceutical composition of claim 1, wherein the X-ray powder diffraction pattern further comprises peaks at about 12.1±0.2, 2θ.

7. The pharmaceutical composition according to claim 1 wherein the X-ray powder diffractogram further comprises peaks at 7.1°±0.2, 8.7°±0.2, and 10.4°±0.2, 2θ.

8. The pharmaceutical composition of claim 1, wherein the rifaximin has an X-ray powder diffraction pattern peaks at about 5.7°±0.2, 6.7°±0.2, 7.1°±0.2, 8.0°±0.2, 8.7°±0.2, 10.4°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2 and 21.5°±0.2, 2θ.

9. The pharmaceutical composition of claim 1, wherein the composition has a water content of between 2.5% and 6.0%.

10. The pharmaceutical composition according to claim 1 wherein the excipients are selected from the group consisting of diluting agents, binding agents, lubricating agents, disintegrating agents, coloring agents and flavoring agents.

11. The pharmaceutical composition according to claim 1, wherein the composition is in a solid form selected from granules, tablets capsules, and powders in sealed packets.

12. A pharmaceutical composition comprising a therapeutically effective amount of rifaximin together with excipients wherein the rifaximin has X-ray powder diffraction pattern peaks at about 7.3°±0.2, 8.2°±0.2 and 10.3°±0.2, 2θ.

13. The pharmaceutical composition of claim 12, wherein the X-ray powder diffraction pattern further comprises peaks at 7.0°±0.2 and 11.1 °±0.2, 2θ.

14. The pharmaceutical composition of claim 12, wherein the X-ray powder diffraction pattern further comprises peaks at about 12.4°±0.2, 8.7°±0.2 and 11.7°±0.2,2θ.

15. The pharmaceutical composition of claim 11, wherein the X-ray powder diffraction pattern further comprises peaks at about 17.5 °±0.2 and 21.5°±0.2, 2θ.

16. The pharmaceutical composition according to claim 11 wherein the X-ray powder diffraction pattern peaks comprises peaks at about 5.7°±0.2, 6.7°±0.2, 7.1°±0.2, 8.0°±0.2, 8.7°±0.2, 10.4°±0.2, 11.3°±0.2, 12.1°±0.2, 17.0°±0.2, 17.3°±0.2, 17.5°±0.2, 18.5°±0.2, 18.8°±0.2, 19.1°±0.2, 21.0°±0.2 and 21.5°±0.2, 2θ.

17. The pharmaceutical composition according to claim 12, wherein the excipients are selected from the group consisting of diluting agents, binding agents, lubricating agents, disintegrating agents, coloring agents and flavoring agents.

18. The pharmaceutical composition according to claim 12, wherein the composition is in a solid form, selected from granules, tablets capsules, and powders in sealed packets.

* * * * *